US008652080B2

(12) United States Patent
Benz et al.

(10) Patent No.: US 8,652,080 B2
(45) Date of Patent: Feb. 18, 2014

(54) APPARATUS AND METHOD OF USE FOR A WRIST EXTENSION BRACE

(75) Inventors: Philip Benz, Portland, OR (US); Robert Henry Niemeyer, III, Tigard, OR (US); Matthew Semler, Portland, OR (US)

(73) Assignee: Semler Technologies, Inc., Milwaukee, OR (US)

( * ) Notice: Subject to any disclaimer, the term of this patent is extended or adjusted under 35 U.S.C. 154(b) by 19 days.

(21) Appl. No.: 13/199,821

(22) Filed: Sep. 9, 2011

(65) Prior Publication Data

US 2012/0071804 A1    Mar. 22, 2012

Related U.S. Application Data

(60) Provisional application No. 61/403,525, filed on Sep. 17, 2010.

(51) Int. Cl.
    *A61F 5/00*    (2006.01)
(52) U.S. Cl.
    USPC ............................................ 602/20; 602/21

(58) Field of Classification Search
    USPC .................... 602/16, 20–22; 128/878–879
    See application file for complete search history.

(56) References Cited

U.S. PATENT DOCUMENTS

| 5,358,471 | A  | * | 10/1994 | Klotz ............................. 602/21 |
| 5,609,570 | A  | * | 3/1997  | Lamont ......................... 602/65 |
| 6,773,410 | B2 | * | 8/2004  | Varn .............................. 602/13 |
| 7,081,102 | B1 | * | 7/2006  | Koetter et al. ................. 602/21 |
| 7,473,234 | B1 | * | 1/2009  | Weltner et al. ................ 602/16 |

* cited by examiner

*Primary Examiner* — Michael A. Brown

(57) ABSTRACT

An apparatus and method of use for a wrist extension brace, intended to be used to position, secure, stabilize, and extend a patient's wrist for the purpose of assisting cannulation of blood vessels in the wrist and forearm. The apparatus generally includes a frame having a fixed dorsiflexion angle and means for cushioning a patient's hand, wrist and forearm and means of attaching such to the wrist extension brace. The method of use includes the steps of attaching the apparatus to a patient's wrist and adjusting it after such attachment.

16 Claims, 5 Drawing Sheets

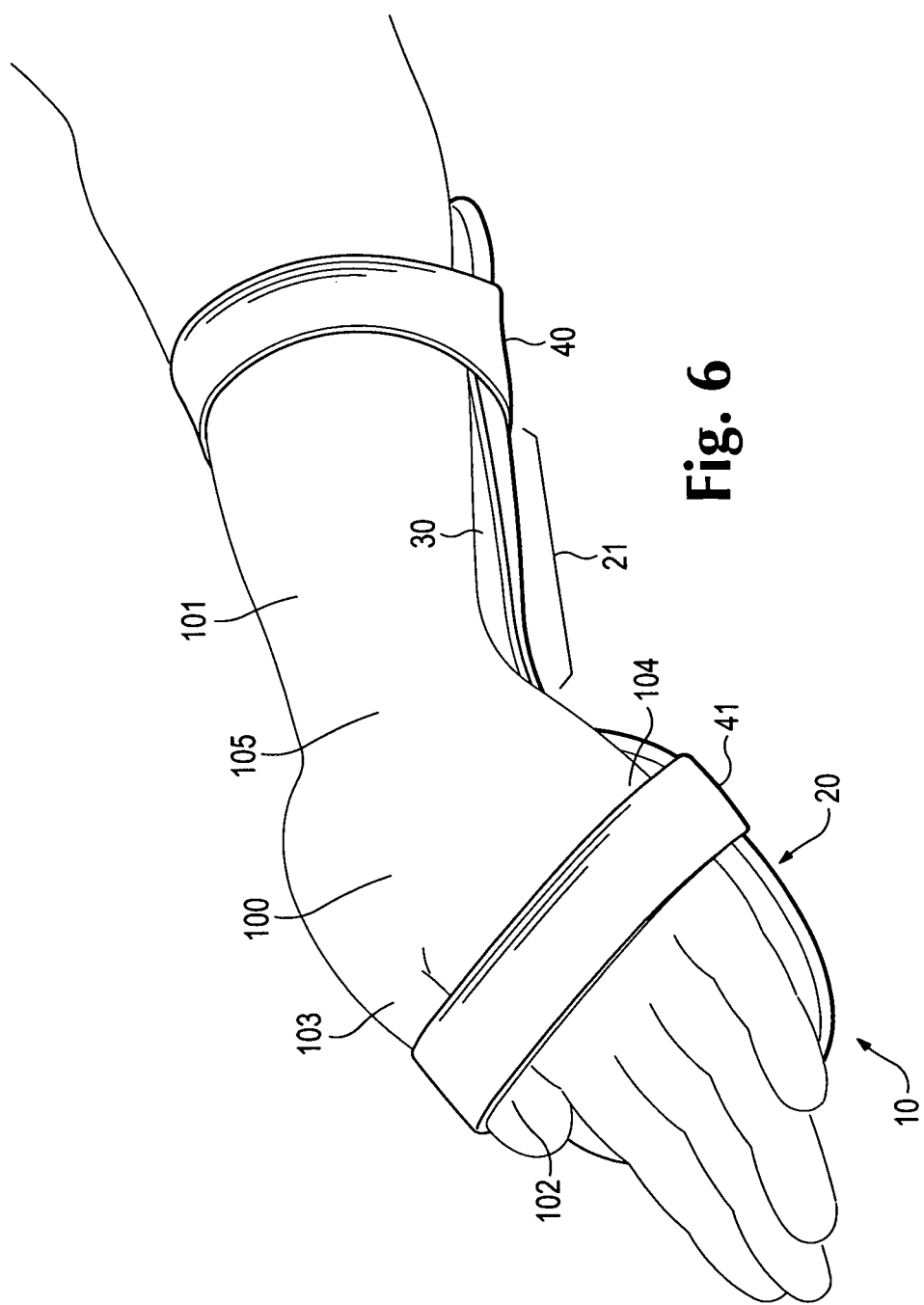

APPARATUS AND METHOD OF USE FOR A WRIST EXTENSION BRACE

Figure 1:
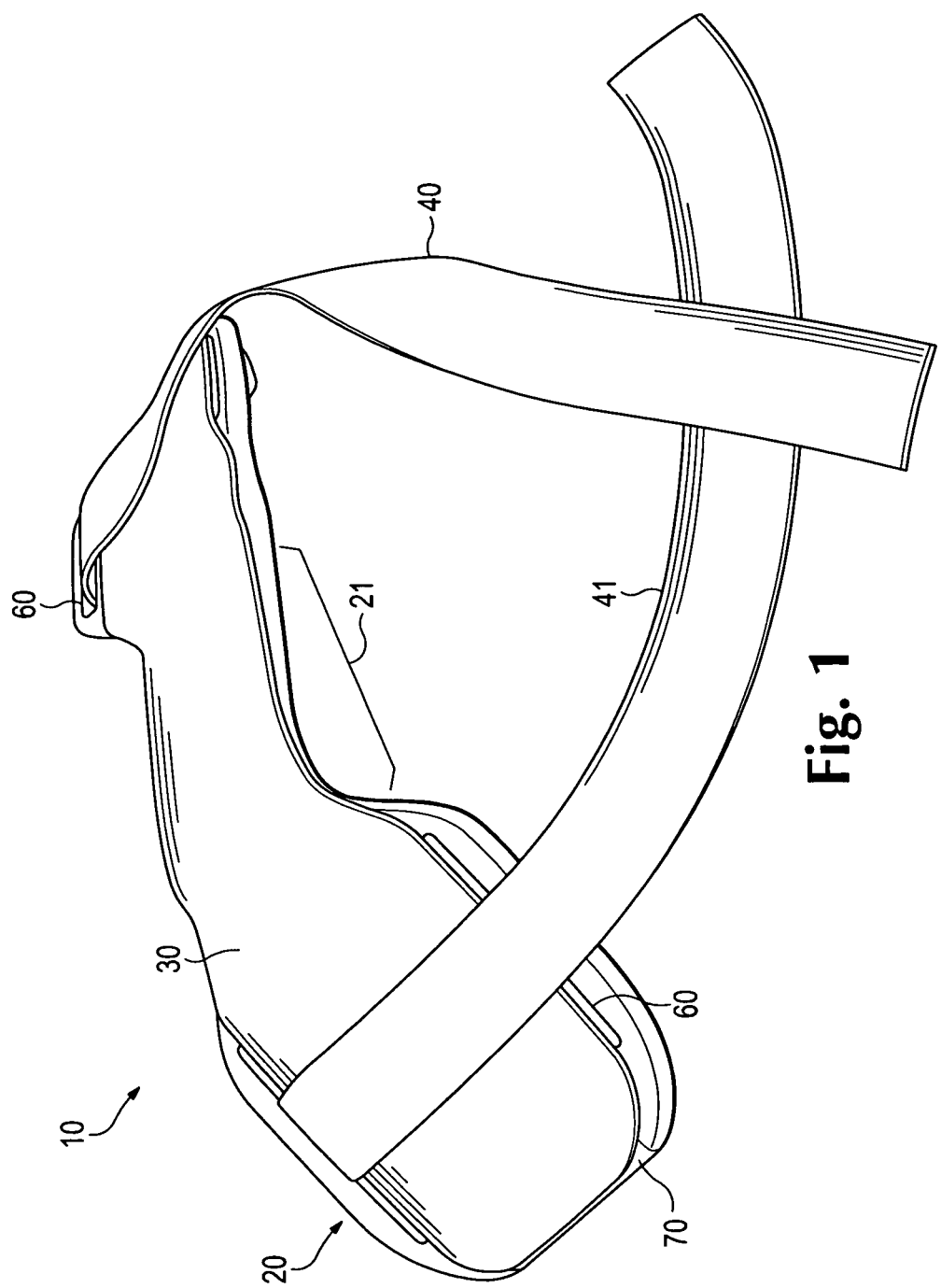

This Non-Provisional Utility patent application claims benefit of Provisional Patent Application 61/403,525, which has a filing date of Sep. 17, 2010.

FIELD OF THE INVENTION

This invention relates generally to wrist braces and supports and, more particularly, to novel apparatuses and methods for positioning, stabilizing, securing and extending the wrist of a human patient for the purpose of cannulating a blood vessel in the wrist and forearm.

BACKGROUND OF THE INVENTION

Cannulation of patients' blood vessels occurs for many reasons, including catheterization for the purpose of inserting catheters for imaging and repairing coronary and other arteries, inserting indwelling lines for the purpose of monitoring the patient, for example to obtain continuous blood pressure or measure blood gasses, or for infusing medications. Such cannulation involves locating a blood vessel in which to create a puncture and then inserting a cannula, which may be sheaths for catheterizations or arterial or venous "lines" for monitoring (these may also be known as "art-lines" or "a-lines"), in some cases for an extended period of time. Such sheaths or lines may also provide vascular access for other procedures, for example, drawing blood, inserting a pacemaker lead or performing electrophysiology tests. Blood vessels commonly used for these purposes include the femoral, brachial, jugular, subclavian and radial arteries and veins. The present invention relates to cannulation of the blood vessels in the wrist, more particularly the radial artery or vein.

Immediately prior to cannulating the radial artery, the operator, who is a medical professional, extends the patient's wrist so as to put it into dorsiflexion. Dorsiflexion of the wrist results in lengthening the vessels therein, thereby making them more taut and less susceptible to movement when accessing the vessel for the purpose of puncturing it and inserting a cannula. The radial artery in particular tends to "roll" or move less when performing the puncture, when it is thusly lengthened. It is also thought that sometimes the vessel moves closer to the skin surface when the wrist is put into dorsiflexion. A dorsiflexion angle in the range of 20° to 45° is thought to provide optimal extension for this purpose.

The patient's hand and forearm are also stabilized prior to cannulation, so that the opportunity for the wrist to move is minimized. The hand is usually placed with the dorsal surface facing down, so that the palmar aspect faces up. In this position, the hand naturally tends to pronate, which causes the area of the forearm to be punctured to often be positioned at a disadvantageous angle relative to the longitudinal axis of movement of the needle used to initially gain vascular access.

Properly extending the wrist into dorsiflexion and securement of the forearm and hand such that the puncture site is stable and facing upward with the proper aspect exposed are therefore requirements that must be addressed for safe, successful cannulation to occur.

Use of materials such as rolled up gauze, rolled up towels and surgical drapes, adhesive tape, and other disposable soft goods are often employed to address these requirements. For catheterizations the wrist is often strapped or taped to an arm-board attached to the procedure table. When inserting a-lines for monitoring, cardboard or other relatively stiff materials are often used in an attempt to address these requirements. Increasingly, braces specifically designed to address these requirements have been developed, including the Hand-Aid product marketed by Kimberly-Clark. Though somewhat effective, the Hand-Aid does not provide good stability or securement since it has rounded ends that encourage side-to-side rolling when placed on a flat surface, and also permits rolling of the forearm and hand when it is deployed onto the patient. Further, it has a relatively shallow dorsiflexion angle.

BRIEF SUMMARY OF THE INVENTION

A useful tool for stabilizing, securing and extending the hand, wrist and forearm of a patient whose blood vessels in that area are about to be cannulated would have the following characteristics: i) usable for the varied usage environments including cardiac catheterization or interventional radiology laboratory, where the patient's arm, with a brace attached, would be secured to an arm-board; ii) provide stability by avoiding pronation or rolling of the forearm, wrist and hand within the brace; iii) provide stability by avoiding rolling of the brace on the arm-board or other flat surface to which it may be attached; iv) usable for critical care nursing, clinic, hospital transport bed, and surgery environment by providing compact size and shape, and comfortable contours; v) provide proper wrist extension; vi) be quick and easy to deploy; vii) be comfortable for the patient.

The present invention, to be known as the "Brace", is intended to be used to position, secure, stabilize, and extend a patient's wrist for the purpose of assisting cannulation of blood vessels in the wrist and forearm. For example, this may be employed when inserting an arterial or venous line or a sheath or catheter into a blood vessel of the wrist or forearm. More particular examples include inserting an arterial line into a patient's radial artery for the purpose of monitoring certain signs, including continuous blood pressure or blood gasses, or when inserting a sheath into such radial artery to provide access for catheters.

Use of the Brace will make the process of achieving a puncture into a blood vessel in the wrist or forearm easier and safer. When deployed onto a patient, the Brace device puts the wrist into dorsiflexion, which lengthens the vessels therein, thereby making them more taut and less susceptible to movement when accessing the vessel. Thus the Brace helps to reduce opportunity for misplaced punctures.

In addition to its wrist extension feature, the Brace includes features for stabilizing the patient's hand, wrist and forearm during and after cannulation. Composed at least partially of a rigid material to enable a consistent dorsiflexion angle and stable securement. The hand is secured to the Brace in a fashion so as to hold it flat, with minimal if any opportunity for pronation. This is caused by the hand strap extending from the proximal phalanx of the thumb or the metacarpophalangeal joint, to be known as the "MCP", of the thumb across the palm of the hand to the MCP or proximal phalanges of the little finger. When used for catheterization procedures using the radial artery in a cardiac catheterization laboratory, the Brace, deployed onto the hand, is often secured on to an arm board with a strap. The arm board is attached to the procedure table and provides a resting place for the patient's arm. The bottom surface of the Brace frame has flat surfaces extending along the width at each end so that it stays flat on the Arm board, with minimal if any opportunity for rolling side to side. Further, the Brace may remain deployed onto the patient following completion of the cannulation procedure, concurrently with a hemostatic device that may be deployed onto the patient's wrist during and after removal of the cannula for the purpose of achieving hemostasis at the site from which the cannula was removed. Such hemostatic devices, for example, the RadAR (Advanced Vascular Dynamics, Portland, Oreg., USA) or TR-Band (Terumo, Tokyo, Japan) devices may be in the form of a strap or bracelet that attaches around the wrist to provide external compression for the purpose of achieving such hemostasis. The tip of such a device may be threaded around the Brace or between the Brace and dorsal surface of the patient's forearm or wrist, and then secured and adjusted. The shape of the Brace may include a narrower width in its middle section to facilitate such hemostatic device deployment.

The Brace may also be deployed onto patients for monitoring patients in their hospital or clinic beds, since the shape of the Brace permits the hand and forearm to comfortably rest wherever the patient desires to place it. Thus the Brace provides the flexibility of having either proper securement and stability when placed on a flat surface, for example on an arm-board, or comfortable placement when it is desired that the patient be able to move their forearm and hand and place it, for example on their lap or next to them in the confines of a hospital or clinic bed while restricting movement of the wrist.

The Brace has a top surface and a bottom surface, and a front end and a back end, and a "dorsiflexion angle". When deployed, this fixed, non-changeable angle, selected generally from the range of 10° to 60° or more particularly 20° to 45°, extends the patient's wrist into dorsiflexion. The brace may include a rigid frame, which has structural features including ribs to provide sufficient strength and rigidity to prevent breakage and excessive flexing or twisting. Further, the frame has stabilization feet, features to prevent the brace, with the patient's hand attached, from rolling when placed on a flat surface, i.e. an armboard used during a catheterization procedure. These may include flat surfaces at the front and back ends of the frame, or a flat strut extending between the front and back ends of the frame. At least one optional tie-down hole may also be included, which extends through the frame at its perimeter. A narrowed waist may also be included in the middle area of the frame so as to enable devices to be deployed around the wrist at the end of the cannulation procedure to more easily enable hemostasis; when the cannulas are removed or other manipulations are made in the cannulation area. Such narrowed waist avoids interference with components of such devices, making their deployment easier. One or more ribs may optionally be included in the construction of a frame to enable rigidity and torsional stability while at the same time minimizing consumption of materials in its construction.

Optionally, at least one arm-board strap may be threaded through the tie-down holes for the purpose of wrapping around an arm board on which the Brace, with the patient's hand attached, is placed, e.g. at time of a catheterization procedure. These tie-down holes can also be used to help guide at least one securement strap, which hold the patient's hand in the Brace.

An optional cushion pad having generally the same shape as the frame, or simply a generally rectangular or oval shape, is placed on top of the frame to provide a cushion between the frame and the patient's hand for the purpose of patient comfort. The cushion pad, if formed separately from the frame, covers the frame and is composed of a pliable material, which is attached to the frame. Such attachment may be achieved by using adhesive or a hook-and-loop means, e.g. Velcro, or other means. Alternatively the cushion pad may be formed as a unitary part of the frame.

The frame has attachment means, e.g. Velcro, on its underside for attaching at least one securement strap. A preferred embodiment may include two securement straps, using Velcro or other similar means for attachment, to secure the patient's hand and forearm to the Brace device. A forearm strap secures the forearm to the Brace. A hand strap secures the hand to the Brace. The straps attach to the frame using the attachment means. Other examples of attachment means include snaps, hooks, or holes with which to attach the straps. Such attachment means may further enable subsequent removal and replacement of the cushion pad and straps onto the frame.

The method of use of the Brace is that it is deployed onto the patient in advance of a cannulation procedure. The hand is placed onto the Brace with its palmar aspect facing up and the dorsal aspect placed flat, directly onto the Brace in a fashion familiar to clinicians performing these cannulation procedures. The dorsal aspects of the patient's wrist and forearm are also placed against the cushion pad. Those skilled in the art of cannulating blood vessels in patient's arm will have a thorough understanding of the mechanics and anatomy involved in this procedure.

The hand, wrist and forearm is then secured to the Brace. The hand strap extends generally diagonally across the palm of the hand, from the thumb MCP or thumb proximal phalanx bone, crossing the little finger MCP or phalanges, to hold the hand flat on the Brace. The forearm strap is wrapped around the forearm proximal to the wrist joint. By placing the hand strap in this fashion, the patient's hand is prevented from rolling and counters the natural tendency of the hand to pronate when placed in the palm-up position.

The forearm and hand straps are then firmly but removably secured using the attachment means, which in a preferred embodiment may be located on the underside of the frame. Tie-down holes may be used to guide and secure the straps.

The Brace, with the patient's hand firmly secured in place, is then placed onto the arm board. In a preferred embodiment, an optional arm board strap is wrapped across the patient's hand (across the fingers), and around the bottom of the arm board, to be secured to an attachment means on the frame or on itself. In some instances, the Brace will not be secured to an arm board at the discretion of the cath lab staff. Tie-down holes may be used to guide and also to secure the arm-board strap.

Preparation of the access site may be performed following deployment of the Brace device onto the patient.

In the case that the Brace is used for placement of an arterial or venous line that will stay in place for an extended period of time, the Brace may be deployed as described above, with an additional activity performed following such placement comprising: loosening the hand, placing a separate padding material between the dorsal surface of the hand and the Brace to decrease the dorsiflexion angle and then re-securing the hand, for purposes of patient comfort.

It will be understood by those skilled in the art that, although the following drawings and Detailed Description of the Invention disclose further aspects and advantages of the Brace and its method of use, and describes preferred embodiments, the present invention is not intended to be limited only to these preferred embodiments. It will be apparent that other changes in form and detail may be made therein without departing from the spirit and scope of the invention.

BRIEF DESCRIPTION OF THE SEVERAL DRAWINGS

FIG. 1—A perspective view of the Brace 10 shows a cushion pad 30 placed on the top surface of the frame 20, included in which tie-down holes 60 and to which are attached a forearm strap 40, a hand strap 41. At the front end of the frame 20 is shown a front stabilization foot 70, and in the middle of the frame 20 is shown the narrowed waist 21.

Figure 2:
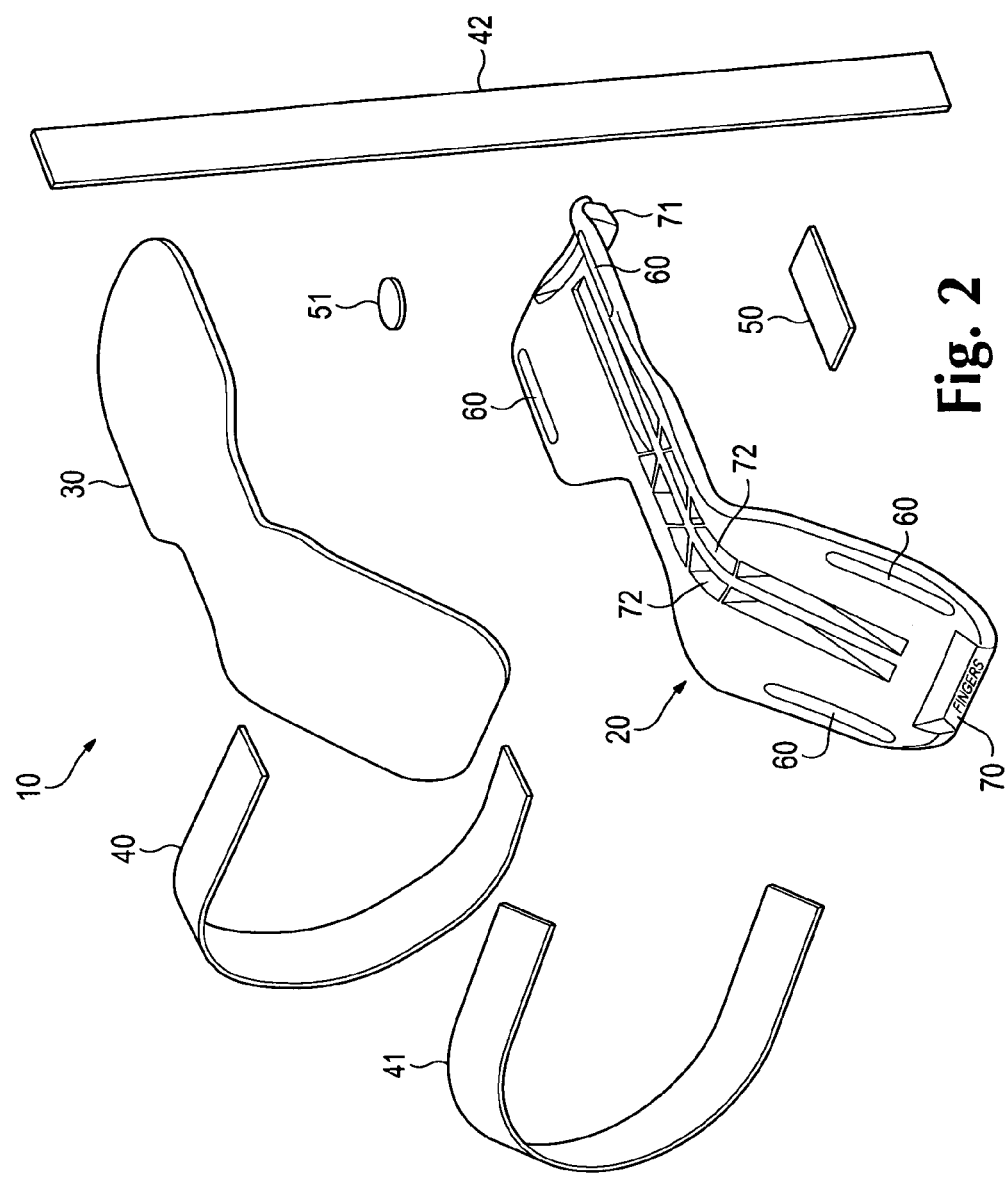

FIG. 2—A perspective exploded view of the Brace 10 shows attachment means 50 and 51, for example adhesively-attached pieces of Velcro hook material, to be placed on the bottom and top surfaces of the frame 20, respectively. A front stabilization foot 70 and a rear stabilization foot 71 are also shown on frame 20 at the front and rear ends, respectively. Structural ribs 72 are also shown integrally formed into the frame 20. Also shown are the tie-down holes 60, the pad 30, the forearm strap 40, the hand strap 41 and an arm-board strap 42.

Figure 3:
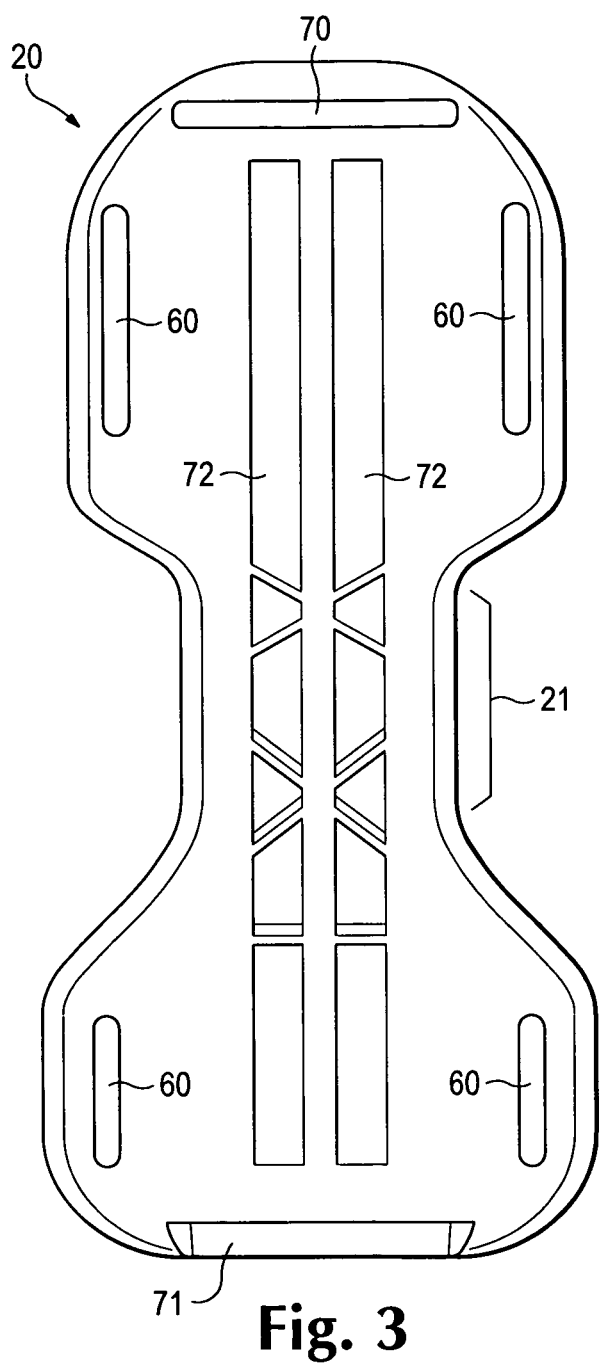

FIG. 3—A bottom view of the frame 20 shows the front stabilization foot 70 and rear stabilization foot 71, both of which lie flat to provide overall stability when the Brace 10 is placed onto a flat surface, for example an arm-board. Also shown is a narrowed waist 21 of the frame 20 and structural ribs 72 and tie-down holes 60 integrally formed into the frame 20, the narrowed waist 21 having a symmetrical shape as shown in this view.

Figure 4:
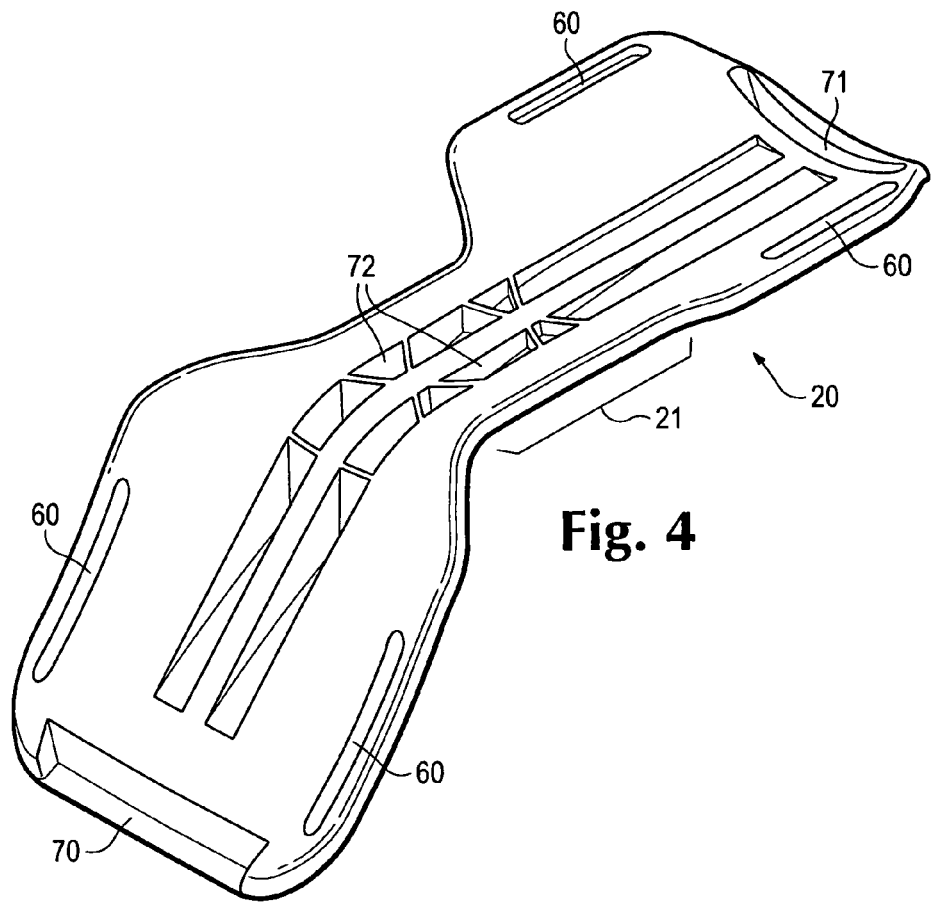

FIG. 4—A perspective view of the frame 20, shows a front stabilization foot 70 and rear stabilization foot 71, which may have flat edges at the tips of the frame 20 so as to provide a stable platform by preventing rocking side to side. Also shown are tie-down holes 60 located along the perimeter of the frame 20, the narrowed waist 21 and ribs 72 integrally formed into the frame 20.

Figure 5:
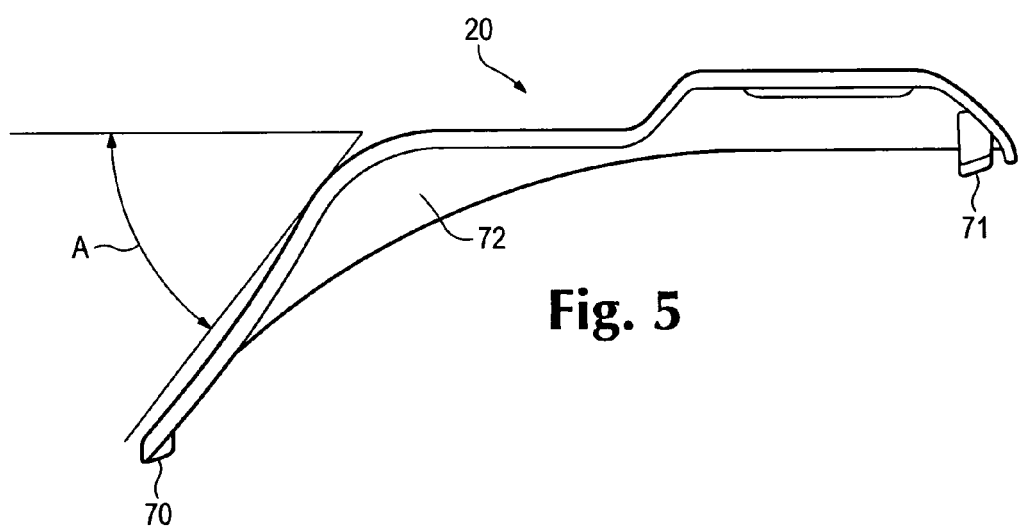

FIG. 5—A side view of the frame 20 shows the locations of the front stabilization foot 70 and rear stabilization foot 71 at the front and rear ends of the frame 20, respectively. In addition, the dorsiflexion angle A is shown. In a preferred embodiment the dorsiflexion angle A is between 10° and 60°, more particularly between 20° and 45°. A structural rib 72 is shown integrally formed into the frame 20.

FIG. 6—A perspective view of the Brace 10 as deployed shows a hand 100 placed onto the Brace 10 with its dorsal surface placed flat onto the cushion pad 30. The forearm strap 40 is shown secured around the forearm 101 and the hand strap 41 is shown secured around the hand 100. Notably, the hand strap 41 wraps around the thumb proximal phalanx 102 and extends across the palm of the hand 100 and around the little finger MCP 104. Alternatively, the hand strap 41 can wrap around the thumb MCP 103 instead of the thumb proximal phalanx 102. The forearm 101, up to the wrist 105, lies over the cushion pad 30 covering the narrowed waist 21 of the frame 20.

DETAILED DESCRIPTION OF THE INVENTION

The frame 20, in the embodiment as shown in FIGS. 2, 3, 4 and 5, is made as a single rigid unitary component having no moving parts and may be composed of a generally rigid material, for example: a thermoplastic such as a polystyrene, polyethylene, polypropylene, nylon or polycarbonate or ABS; a fiber material; or, a metal. The attachment means 50 or 51 may be an adhesive, for example: a double-sided adhesive tape; or, a hook-and-loop material such as Velcro. The attachment means 50 or 51 may be permanently attached to the frame 20, or be formed as a unitary element of the frame 20, for example, it may be molded into the frame 20 during injection molding. The cushion pad 30 may composed of a material, preferably having a characteristic of pliancy and flexibility, for example: a synthetic foam; a hydrogel; a cloth composed of either natural or synthetic fibers; a silicone or similar moldable material; a composite or lamination of more than one material; or, a thermoplastic. The material of the cushion pad 30 may further include the property, on the side contacting the patient skin, of wicking away moisture from the skin. The cushion pad 30 may further include on one side a loop material to removably attach to hook material adhesively placed onto or molded into the frame 20. The straps 40 and 41 may further include on one side a loop material to removably attach to hook material, for example, attachment means 51, adhesively placed onto or molded into the frame 20. The forearm strap 40 and hand strap 41 may be composed of a material, preferably having a characteristic of flexibility, for example: a synthetic foam; a hydrogel; a cloth composed of either natural or synthetic fibers; a composite or lamination of more than one material; or, a thermoplastic. The straps 40 and 41 may further include on one side a loop material' to removably mate with hook material located on the frame 20, for example, attachment means 50. The arm-board strap 42 may be composed of a material, preferably having a characteristic of flexibility, for example: a synthetic foam; a fabric composed of natural or synthetic fibers; a composite or lamination of more than one material; or, a thermoplastic. The material of arm-board strap 42 may further include the characteristic of a hook-and-loop material wherein the hook portion is on one side and the loop portion is on the opposite side such that the arm-board strap 42, when wrapped around the hand 100, Brace 10 and arm-board to secure it in place, for example in the catheterization laboratory, it attaches to itself. Construction of these components may be separately, or in combination as a unitary piece. If constructed and provided separately from the frame 20, the cushion pad 30 and straps 41 and 42 may be provided unattached to the frame,20 such that the user would assemble these components using the attachment means 50 and 51. In this embodiment, the cushion pad 30 would have a shape that conforms to the outline of the frame 20 or alternatively it may have a generally rectangular or oval shape.

When cannulating a vessel in a patient's wrist 105 for the purpose of a catheterization procedure, the hand 100 and forearm 101 are placed onto the Brace 10 with the hand's 100 palmar aspect facing up and the dorsal aspects placed flat, directly onto the cushion pad 30.

The hand 100 is then secured to the Brace 10. The hand strap 41 crosses the distal aspect of the thumb MCP 103, over the palm of the hand 100 and extending generally diagonally from the thumb MCP 103 or the thumb proximal phalanx 102 and across the little finger MCP 104. By placing the hand strap 41 in this fashion, the patient's hand 100 is held flat against the Brace 10 and prevented from rolling, thus countering the natural tendency of a hand to pronate when placed in the palm-up position: The forearm strap 40 is wrapped around the forearm 101. The forearm strap 40 and hand strap 41 are firmly secured by attaching them to the attachment means 50, which in a preferred embodiment may be located on the underside of the frame 20. Tiedown holes 60 may optionally be used to guide the straps 40 and 41. The tie-down holes may also be used to attach the straps 40 and 41 to the Brace 10.

The Brace 10, with the patient's hand 100 firmly secured in place, may then placed at the discretion of the user onto an arm board. In a preferred embodiment, an optional arm board strap 42 is wrapped across the patient's hand 100 (across the fingers), and around the bottom of the arm board, to be secured to an attachment means on the frame or onto itself. In some instances, the Brace 10 may not be secured to an arm board, at the discretion of the user. Tie-down holes 60 may be used to guide and secure the arm-board strap 42.

The Brace 10 may remain deployed onto the patient following completion of the cannulation procedure, concurrently with a separately provided hemostatic device (for example, the RadAR or TR-Band devices) that may be deployed onto the patient's wrist 105 during and after removal of the cannula for the purpose of achieving hemostasis at the site from which the cannula was removed. The tip of such a device may be threaded around the outside surface of the frame 20 or between the pad 30 or frame 20 and the dorsal surface of the patient's forearm 101 or wrist 105. The hemostatic device may then be secured. The shape of the Brace 10 or more particularly frame 20 may include a narrowed waist 21 generally in the middle section to facilitate such hemostatic device deployment, the narrowed waist 21 having a symmetrical shape as shown in the circumference of the frame 20 in FIG. 3.

When placing arterial lines or venous lines into a vessel in a patient's wrist 105, the hand 100 and forearm 101 are placed onto the Brace 10 with the hand's 100 palmar aspect facing up and the dorsal aspects placed flat, directly onto the cushion pad 30.

The hand 100 and forearm 101 is then secured to the Brace with the hand strap 41 and forearm strap 40 as described in the foregoing. Following arterial line placement, the hand strap 41 may at the discretion of the user be released and a padding, which may optionally be included with the Brace 10, placed between the dorsal surface of the hand 100 and the cushion pad 20 to decrease the dorsiflexion angle A, for the purpose of increasing patient comfort. The hand strap 41 would then be re-secured to hold the hand 100 in place.

We claim:

1. A wrist extension brace including at least a rigid frame, a cushion pad, and at least one strap for use in extending a wrist and securing and stabilizing a hand, a forearm and said wrist for the purpose of assisting in the cannulation of a blood vessel in said wrist, the frame having a single fixed, non-changeable dorsiflexion angle selected from the range of 10° to 60°, and a narrow waist located generally in the center area of the frame, the narrowed waist having a symmetrical shape.

2. The frame of claim 1, which further includes at least one stabilization foot, the foot having a flat edge on the bottom surface at an end of the frame.

3. The frame of claim 1, which further includes at least one integrally formed structural rib.

4. The frame of claim 1, which further includes at least one tie-down hole.

5. The frame of claim 1, which further includes means, formed as a unitary element of said frame, for removably attaching at least one of the cushion pad or strap.

6. The at least one strap of claim 1, which further includes at least one hand strap.

7. The at least one strap of claim 1, which more particularly includes at least one arm-board strap.

8. The at least one strap of claim 1, which more particularly includes at least one forearm strap.

9. The single fixed, non-changeable dorsiflexion angle of claim 1, which is more particularly selected from the range of 20° to 45°.

10. The cushion pad of claim 1, which more particularly has a shape that conforms to the circumference of the frame.

11. The cushion pad and at least one strap of claim 1, which are more particularly removably attachable to the frame.

12. The cushion pad and at least one strap of claim 11, the material of which includes on at least one side loop material with which to removably attach to hook material.

13. A method of use of a wrist extension brace that includes at least one of a frame, a cushion pad, and at least an arm strap and forearm strap, the frame having a fixed, non-changeable dorsiflexion angle selected from the range of 10° to 60°, and a narrow waist located generally in the center area of the frame, the narrowed waist having a symmetrical shape, the method including the following steps: i) a hand is placed onto said brace with its palmar aspect facing up and its dorsal aspect placed flat, directly onto the brace; ii) the hand is secured onto the brace by placing a hand strap such that it extends across the palm of the hand, from the thumb MCP or thumb proximal phalanx, crossing the little finger MCP to hold the hand flat on the brace, and the forearm is secured onto the brace by placing a forearm strap such that it crosses over the forearm; iii) the forearm and hand straps are firmly secured to the brace.

14. The method of use of claim 13, which further includes an additional subsequent step of using an arm-board strap to secure the brace, with the hand placed in it, onto an arm-board or other flat surface.

15. The method of use of claim 13, which, at time of and following removal of a cannula from the patient's vessel subsequent to placement of the hand onto the brace, further includes an additional subsequent step of deploying a hemostatic device around the patient's wrist.

16. A frame, included in a wrist brace for use in extending a wrist and securing and stabilizing a hand, a forearm and said wrist for the purpose of assisting in the cannulation of a blood vessel in said wrist; the frame having a fixed dorsiflexion angle selected from the range of 10° to 60°, a narrow waist located generally in the center area of the frame, the narrowed waist having a symmetrical shape, the frame further including a narrow waist having a symmetrical shape located generally in its center area, at least one structural rib, at least one stabilization foot, said foot having a flat edge located at an end of the frame on its bottom surface, and means for removably attaching at least one of a separate cushion pad and strap.

* * * * *